(12) United States Patent
Sageman et al.

(10) Patent No.: US 8,124,598 B2
(45) Date of Patent: Feb. 28, 2012

(54) 7-KETO DHEA FOR PSYCHIATRIC USE

(76) Inventors: Sharon Sageman, New York City, NY (US); Richard P. Brown, Kingston, NY (US)

( * ) Notice: Subject to any disclaimer, the term of this patent is extended or adjusted under 35 U.S.C. 154(b) by 240 days.

(21) Appl. No.: 11/851,761

(22) Filed: Sep. 7, 2007

(65) Prior Publication Data

US 2008/0070879 A1 Mar. 20, 2008

Related U.S. Application Data

(60) Provisional application No. 60/844,479, filed on Sep. 14, 2006.

(51) Int. Cl.
*A61K 31/56* (2006.01)
*C07J 1/00* (2006.01)

(52) U.S. Cl. ........................ 514/177; 552/650
(58) Field of Classification Search .................. 514/177; 552/650
See application file for complete search history.

(56) References Cited

U.S. PATENT DOCUMENTS

| | | |
|---|---|---|
| 4,835,147 A | 5/1989 | Roberts |
| 4,839,177 A | 6/1989 | Colombo et al. |
| 4,891,223 A | 1/1990 | Ambegaonkar et al. |
| 5,397,574 A | 3/1995 | Chen |
| 5,399,358 A | 3/1995 | Baichwal et al. |
| 5,399,359 A | 3/1995 | Baichwal |
| 5,399,362 A | 3/1995 | Baichwal et al. |
| 5,419,917 A | 5/1995 | Chen et al. |
| 5,422,123 A | 6/1995 | Conte et al. |
| 5,456,921 A | 10/1995 | Mateescu et al. |
| 5,458,005 A | 10/1995 | Perelshteyn |
| 5,458,887 A | 10/1995 | Chen et al. |
| 5,458,888 A | 10/1995 | Chen |
| 5,464,633 A | 11/1995 | Conte et al. |
| 5,472,708 A | 12/1995 | Chen |
| 5,512,297 A | 4/1996 | Baichwal |
| 5,585,371 A | 12/1996 | Lardy |
| 5,603,956 A | 2/1997 | Mateescu et al. |
| 5,641,766 A | 6/1997 | Lardy |
| 5,686,113 A | 11/1997 | Speaker et al. |
| 5,702,727 A | 12/1997 | Amkraut et al. |
| 5,705,585 A | 1/1998 | Hogan, Jr. |
| 5,707,983 A | 1/1998 | Lardy |
| 5,725,883 A | 3/1998 | Staniforth et al. |
| 5,756,264 A | 5/1998 | Schwartz et al. |
| 5,770,580 A | 6/1998 | Ledley et al. |
| 5,773,025 A | 6/1998 | Baichwal |
| 5,789,375 A | 8/1998 | Mukae et al. |
| 5,792,751 A | 8/1998 | Ledley et al. |
| 5,824,638 A | 10/1998 | Burnside et al. |
| 5,834,023 A | 11/1998 | Chen |
| 5,837,379 A | 11/1998 | Chen et al. |
| 5,856,435 A | 1/1999 | Bazile et al. |
| 5,885,616 A | 3/1999 | Hsiao et al. |
| 5,897,876 A | 4/1999 | Rudnic et al. |
| 5,904,936 A | 5/1999 | Huille et al. |
| 5,912,013 A | 6/1999 | Rudnic et al. |
| 5,916,595 A | 6/1999 | Chen et al. |
| 5,925,564 A | 7/1999 | Schwartz et al. |
| 5,952,004 A | 9/1999 | Rudnic et al. |
| 5,962,566 A | 10/1999 | Grandfils et al. |
| 5,981,467 A | 11/1999 | Hogan, Jr. |
| 5,985,353 A | 11/1999 | Lawton et al. |
| 6,002,817 A | 12/1999 | Kopelman et al. |
| 6,004,582 A | 12/1999 | Faour et al. |
| 6,007,845 A | 12/1999 | Domb et al. |
| 6,077,541 A | 6/2000 | Chen et al. |
| 6,086,881 A | 7/2000 | Frey et al. |
| 6,096,340 A | 8/2000 | Chen et al. |
| 6,099,859 A | 8/2000 | Cheng et al. |
| 6,099,862 A | 8/2000 | Chen et al. |
| 6,103,263 A | 8/2000 | Lee et al. |
| 6,106,862 A | 8/2000 | Chen et al. |
| 6,110,498 A | 8/2000 | Rudnic et al. |
| 6,121,005 A | 9/2000 | Fournier et al. |
| 6,149,868 A | 11/2000 | Natan et al. |
| 6,159,445 A | 12/2000 | Klaveness et al. |
| 6,180,415 B1 | 1/2001 | Schultz et al. |
| 6,187,559 B1 | 2/2001 | Steed et al. |
| 6,214,560 B1 | 4/2001 | Yguerabide et al. |

(Continued)

FOREIGN PATENT DOCUMENTS

CN 1552331 A * 12/2004

(Continued)

OTHER PUBLICATIONS

Sharp, Current Pain and Headache Reports, 2004, Science Inc., vol. 8, pp. 111-115.*

(Continued)

*Primary Examiner* — Sreeni Padmanabhan
*Assistant Examiner* — Sarah Pihonak
(74) *Attorney, Agent, or Firm* — Kilpatrick Townsend & Stockton LLP

(57) ABSTRACT

The present invention comprises novel methods for the use of compositions comprising 7-keto DHEA for treating psychiatric conditions. These methods include administering an effective amount of a composition comprising 7-keto DHEA in an acceptable carrier, alone or in combination with other psychiatric drugs, such as analgesic agents, anticonvulsants, anti-anxiety agents, antidepressants, anti-panic agents, antipsychotic agents, bipolar agents, psychostimulants to reduce or ameliorate symptoms of a psychiatric condition. This method may be used alone or as an adjunctive treatment for treating a wide variety of psychiatric conditions such as stress disorders, anxiety disorders and depressive disorders.

12 Claims, No Drawings

U.S. PATENT DOCUMENTS

| | | | |
|---|---|---|---|
| 6,217,864 | B1 | 4/2001 | Coffino et al. |
| 6,217,901 | B1 | 4/2001 | Perrott et al. |
| 6,217,912 | B1 | 4/2001 | Park et al. |
| 6,248,724 | B1 | 6/2001 | Moore et al. |
| 6,262,032 | B1 | 7/2001 | Tocque |
| 6,262,129 | B1 | 7/2001 | Murray et al. |
| 6,265,546 | B1 | 7/2001 | Cohen et al. |
| 6,268,222 | B1 | 7/2001 | Chandler et al. |
| 6,272,262 | B1 | 8/2001 | Kopelman et al. |
| 6,288,040 | B1 | 9/2001 | Muller et al. |
| 6,306,610 | B1 | 10/2001 | Bawendi et al. |
| 6,312,731 | B1 | 11/2001 | Staas et al. |
| 6,316,029 | B1 | 11/2001 | Jain et al. |
| 6,323,989 | B1 | 11/2001 | Jacobson et al. |
| 6,333,051 | B1 | 12/2001 | Kabanov et al. |
| 6,350,515 | B1 | 2/2002 | Lawton et al. |
| 6,361,944 | B1 | 3/2002 | Mirkin et al. |
| 6,368,617 | B1 | 4/2002 | Hastings et al. |
| 6,383,500 | B1 | 5/2002 | Wooley et al. |
| 6,387,329 | B1 | 5/2002 | Lewis et al. |
| 6,395,253 | B2 | 5/2002 | Levy et al. |
| 2003/0092692 | A1 | 5/2003 | Lathe et al. |
| 2004/0248861 | A1* | 12/2004 | Kneller .................. 514/169 |
| 2005/0069593 | A1* | 3/2005 | Zwiefel .................. 424/655 |
| 2005/0089541 | A1 | 4/2005 | Lacoutiere |
| 2006/0154908 | A1* | 7/2006 | Patel et al. .................. 514/171 |
| 2008/0070879 | A1 | 3/2008 | Sageman et al. |
| 2010/0160274 | A1 | 6/2010 | Sageman et al. |

FOREIGN PATENT DOCUMENTS

| | | |
|---|---|---|
| WO | WO9847491 | 10/1998 |
| WO | WO0160375 | 8/2001 |
| WO | WO2004075832 | 9/2004 |

OTHER PUBLICATIONS

Marek et al., The Journal of the American Society for Experimental NeuroTherapeutics, 2005, The American Society for Experimental Therapeutics Inc., vol. 2, pp. 579-589.*

Hirschfeld, Primary Care Companion J Clin. Psychiatry, 2001, Physicians Postgraduate Press, vol. 3, No. 6, pp. 244-254.*

O'Brien et al., British Medical Journal, 2001, British Medical Association, vol. 323, pp. 123-124.*

Berge, Stephen M. et al., "Pharmaceutical Salts," *Journal of Pharmaceutical Sciences*, Jan. 1977, vol. 66, No. 1, pp. 1-19.

Bloch, Miki et al., "Dehydroepiandrosterone Treatment of Midlife Dysthymia," *Biol Psychiatry*, 1999, vol. 45, pp. 1533-1541.

Brady, Kathleen et al., "Efficacy and Safety of Sertraline Treatment of Posttraumatic Stress Disorder," *JAMA*, Apr. 12, 2000, vol. 283, No. 14, pp. 1837-1844.

Charney M.D., Dennis S., Psychobiological Mechanisms of Resilience and Vulnerability: Implications for Successful Adaptation to Extreme Stress, *Am J Psychiatry*, Feb. 2004, 161:2, pp. 195-216.

Davidson, Jonathan R. et al., "Multicenter, Double-blind Comparison of Sertraline and Placebo in the Treatment of Posttraumatic Stress Disorder," *Arch Gen Psychiatry*, May 2001, vol. 58, pp. 485-492.

Davidson, Michael et al., "Safety and pharmacokinetic study with escalating doses of 3-acetyl-7-oxo-dehydroepiandrosterone in healthy male volunteers," *Clin Invest Med*, Oct. 2000, vol. 23, No. 5, pp. 300-310.

Dunner, David L., "Management of Anxiety Disorders: The Added Challenge of Comorbidity," *Depression and Anxiety*, 2001, vol. 13, pp. 57-71.

Fava, Maurizio et al., "Fluoxetine versus sertraline and paroxetine in major depression: tolerability and efficacy in anxious depression," *Journal of Affective Disorders*, 2000, vol. 59, pp. 119-126.

Gurnell, Eleanor M. et al., "Dehydroepiandrosterone replacement therapy," *European Journal of Endocrinology*, 2001, vol. 145, pp. 103-106.

Harvey, Allison G. et al., "The Relationship Between Acute Stress Disorder and Posttraumatic Stress Disorder: A 2-Year Prospective Evaluation," *Journal of Consulting and Clinical Psychology*, 1999, vol. 67, No. 6, pp. 985-988.

Huppert, F. A. et al., Abstract of "Dehydroepiandrosterone (DHEA) supplementation for cognition and well-being," *Cochrane Database Syst Rev*, 2000, Cambridge, UK.

Kaufman, Joan et al., "Comorbidity of Mood and Anxiety Disorders," *Depression and Anxiety*, 2000, vol. 12, Supplement 1, pp. 69-76.

Koren, Danny et al., "Increased PTSD Risk with Combat-Related Injury: A Matched Comparison of Injured and Uninjured Soldiers Experiencing the Same Combat Events," *Am J Psychiatry*, Feb. 2005, 162:2, pp. 276-282.

Lecrubier, Yves, "Comorbidity in Social Anxiety Disorder: Impact on Disease Burden and Management," *J Clin Psychiatry*, 1998, vol. 59, Supp. 17, pp. 33-37.

Lecrubier, Yves, "The Impact of Comorbidity on the Treatment of Panic Disorder," *J Clin Psychiatry*, 1998, vol. 59, Supp. 8, pp. 11-14.

"Longevity & Energy Without Hormonal Side Effect," proHeath Immune Support.com.

Marshall, Randall D. et al., "Efficacy and Safety of Paroxetine Treatment for Chronic PTSD: A Fixed-Dose, Placebo-Controlled Study," *Am J Psychiatry*, Dec. 2001, 158:12, pp. 1982-1988.

Morfin, Robert et al., "Neurosteriod 7-Hydroxylation Products in the Brain," *International Review of Neurobiology*, 2001, vol. 46, pp. 79-95.

Morgan, Charles A. et al., "Relationships Among Plasma Dehydroepiandrosterone Sulfate and Cortisol Levels, Symptoms of Dissociation, and Objective Performance in Humans Exposed to Acute Stress," *Arch Gen Psychiatry*, Aug. 2004, vol. 61, pp. 819-825.

Rasmusson, Ann M. et al., "An Increased Capacity for Adrenal DHEA Release is Associated with Decreased Avoidance and Negative Mood Symptoms in Women with PTSD," *Neuropsychopharmacology*, 2004, vol. 29, pp. 1546-1557.

Rupprecht, R. et al., Abstract of "Neuropsychopharmacological properties of neuroactive steroids," *Steroids*, Jan.-Feb. 1999, 64(1-2), 83-91, Munich, Germany.

Sageman, Sharon et al., "3-Acetyl-7-Oxo-Dehydroepiandrosterone for Healing Treatment-Resistant Posttraumatic Stress Disorder in Women: 5 Case Reports," Letters to the Editor, *J Clin Psychiatry*, Mar. 2006, 67:3, pp. 493-496.

Schmidt, Peter J. et al., "Dehydroepiandrosterone Monotherapy in Midlife-Onset Major and Minor Depression," *Arch Gen Psychiatry*, Feb. 2005, vol. 62, pp. 154-162.

Silverman, Wendy K. et al., "Treating Disorders in Children With Group Cognitive-Behavioral Therapy: A Randomized Clinical Trial," *Journal of Consulting and Clinical Psychology*, 1999, vol. 67, No. 6, pp. 995-1003.

Silverstone, Peter H. et al., "Defining Anxious Depression: Going Beyond Comorbidity," *Can J Psychiatry*, Nov. 2003, vol. 48, No. 10, pp. 675-680.

Wolkowitz, Owen M. et al., "Dehydroepiandrosterone (DHEA) Treatment of Depression," *Biol Psychiatry*, 1997, vol. 41, pp. 311-318.

Wolkowitz, Owen M. et al., "Double-Blind Treatment of Major Depression with Dehydroepiandrosterone," *Am J Psychiatry*, Apr. 1999, 156:4, pp. 646-649.

Yen, Samuel S., "Dehydroepiandrosterone sulfate and longevity: New clues for an old friend," *PNAS*, Jul. 17, 2001, vol. 98, No. 15, pp. 8167-8169.

PCT/US2008/074229 International Search Report and Written Opinion mailed Dec. 22, 2008.

Nachshoni, T. et al., "The effect of DHEA administration on extrapyramidal symptoms in schizophrenia: a randomized double blind placebo controlled trial," *European Neuropsychpharmacology*, Elsevier Science Publishers BV, Amsterdam, NL, Jan. 1, 2005, vol. 15, pp. 135-136.

Strous, R. D. et al., "Dehydroepiandrosterone augmentation in the management of negative, depressive, and anxiety symptoms in schizophrenia," *Archives of General Psychiatry*, Feb. 2003, vol. 60, No. 2, pp. 133-141.

Bonnett, Kenneth et al., "Cognitive Effects of DHEA Replacement Therapy", in *Biologic Role of Dehydropiandrosterone (DHEA)*, Eds. M. Kalimi and W. Regelson, 1990, pp. 65-79, Walter de Gruyter & Co., N.Y.

Maninger, Nicole et al., "Neurobiological and neuropsychiatric effects of dehydroepiandrosterone (DHEA) and DHEA sulfate (DHEAS)", Fronteirs in Neuroendocrinology 2009, 30: 65-91.

European Application No. 08798637.8, Office Action mailed on Aug. 23, 2010, 8 pages.

08798637.8, "EPO Office Action", mailed Apr. 5, 2011.

08798637.8, "EPO Response to Office Action", filed May 24, 2011.

08798637.8, "EPO Response to Office Action", filed Dec. 7, 2010.

* cited by examiner

7-KETO DHEA FOR PSYCHIATRIC USE

PRIOR RELATED APPLICATIONS

The present application claims the benefit of priority to U.S. provisional patent application No. 60/844,479, filed Sep. 14, 2006.

FIELD OF THE INVENTION

The present invention relates to methods of using compositions comprising 3-acetyl-7-oxo-dehydroepiandrosterone (7-keto DHEA) to treat psychiatric conditions. More specifically the present invention relates to methods of using compositions comprising 7-keto DHEA to treat post-traumatic stress disorders and related stress-associated psychiatric conditions.

BACKGROUND

A hundred years ago the major cause of illness was infection. Today a major cause of illness is stress related. Chronic stress affects the hypothalamic-pituitary-adrenal axis and the secretion of glucocorticoids, resulting in neurotoxic effects that play an important role in the brain changes seen in depression and in post traumatic stress disorder.

Psychiatric disorders are debilitating conditions that impair the productivity of otherwise physically healthy individuals. Often, the development is gradual and symptom severity increases undetectably until an individual's functionality is impaired. As an example, chronic severe posttraumatic stress disorder (PTSD) is a common psychiatric disorder with an estimate lifetime prevalence of 7.8%. In certain populations, such as Vietnam combat veterans, the rate of PTSD is 30%. PTSD resulting from early physical and/or sexual abuse is a highly prevalent psychiatric condition in women. PTSD causes persistent functional impairment and emotional distress and generally shows only a limited response to current available psychopharmacologic treatments. Studies also indicate that PTSD will develop in 15% to 25% of trauma victims. Recent studies have shown that physical injury, over and above exposure to the traumatic event increases the risk of PTSD (Koren, *Am J Psychiatry*, 2005; 162:276-282). Certain types of trauma are associated with a very high rate of subsequent development of PTSD. An example of this is rape. PTSD has been shown to occur in 50% of women and 65% of men following rape.

Time-limited responses develop in a large proportion of trauma victims during the first 48-72 hours (acute stress reaction) and to a lesser extent over the first 4 weeks (acute stress disorder). The presence of Acute Stress Disorder signals a need for an immediate preventive intervention since the likelihood of developing PTSD is between 60% and 80% (Harvey, *J Consult Clin Psych*. 1999:67:995-998).

Selective serotonin reuptake inhibitors (SSRIs), the most commonly used and only U.S. Food and Drug Administration-approved treatment for PTSD, have shown a modest treatment effect of between 0.3 and 0.5. (Brady et al, *JAMA*, 2000, 283:1837-1844; Davidson et al., *Arch Gen Psychiatry* 2001:58:485-492; and Marshall et al., *Am J Psychiatry*, 2001: 158:1982-1988). Consequently, many of these patients remain quite ill and impaired in their functioning, even after numerous trials and years on medication treatment. Despite the common occurrence of this disorder, pharmacologic treatment studies are limited.

Depression, anxiety, and stress share biological pathways and symptoms of these conditions frequently occur together in clinical practice. Recent estimates show that close to 60% of patients with Major Depressive Disorder (MDD) have a co-morbid anxiety disorder (Silverstone et al., *Can J Psychiatry* 2003:48:675-680). In almost every diagnostic category of anxiety disorders, nearly 50% of patients are reported to have a co-morbid depressive disorder (Dunner, *Depress Anxiety*. 2001; 13:57-71).

Fava et al. (*J Affect Disord* 2000; 59:119-126), reported that Generalized Anxiety Disorder preceded depression 63% of the time. Post Traumatic Stress Disorder (PTSD) has been shown to precede Major Depressive Disorder one half to two thirds of the time (Kaufman and Chamey, *Depress Anxiety*. 2000; 12 Suppl 1:69-76). Time trend analysis of the U.S. National Comorbidity Survey shows that the onset of an anxiety disorder results in a fairly persistent risk for the development of MDD and that an increased risk of MDD persists for many years after the onset of an anxiety disorder.

Patients with co-occurring depression and anxiety disorders are common and tend to experience greater functional impairment, higher symptom severity and poorer prognosis than those with either disorder alone (Kaufman and Chamey, *Depress Anxiety* 2000; 12, Supp. 1:69-76; Lecrubier, *J Clin Psychiatry*. 1998; 59 Suppl 17:33-38; Lecrubier, *J Clin Psychiatry*. 1998; 59 Suppl 8:11-4; discussion 15-16). As a result, these patients often require more aggressive and multiple treatment modalities in order to effectively treat both conditions. Dehydroepiandrosterone (DHEA) is a compound that has been shown to have actions on certain psychiatric conditions. One open series, (Wolkowitz et al. *Biol Psychiatry* 1997; 41:311-318) and 3 placebo-controlled, double-blind, randomized trials (Schmidt et al., *Arch Gen Psychiatry* 2005; 62:154-162, Wolkowitz et al. *Am J Psychiatry* 1999; 156:646-649, Bloch et al. *Biol Psychiatry* 1999; 45:1533-1541) have supported the effectiveness of DHEA in midlife major and minor depression or dysthymia. Several recent reviews have also discussed data on DHEA to enhance memory, cognition, sexual functioning, and well-being in healthy elderly individuals and in patients with adrenal insufficiency. (Gurnell et al. *Eur J Endocrinol* 2001; 145:103-106, Yen S S C., *PNAS* 2001:98:8167-8169). Unfortunately, DHEA is aromatized into testosterone or estrogen and therefore has risks associated with its use.

DHEA appears to have similar actions on both males and females. The study by Rasmusson et al. (*Neuropsychopharmacology* 2004; 29:1546-1557) of 13 women with chronic PTSD showed that a higher level of DHEA in response to activation by adrenocorticotropic hormone was associated with less severe PTSD symptomotology and that a higher ratio of peak DHEA to cortisol was associated with less-severe negative mood symptoms. Morgan and colleagues' study of 25 elite special operations solders during prolonged and extreme training stress showed that subjects who reported fewer symptoms of dissociation and exhibited superior military performance had significantly higher ratios of DHEA sulfate to cortisol (Morgan et al., *Arch Gen Psychiatry* 2004; 61:819-825).

DHEA and its sulfate ester (DHEA-S) are produced in human adrenal glands beginning at about 7 years of age. DHEA-S is the most abundant steroid (14 mg/l) in the blood plasma of humans at age 20 to 30 years, and decreases steadily to about one-tenth that concentration at age 70 to 80 years. Because levels of DHEA and general health decline with age, it has been postulated that DHEA replacement may help to maintain a more youthful state. DHEA is an intermediate in the biologic conversion of cholesterol to androgens and estrogens. DHEA can be hydroxylated in tissues to produce both 7 alpha and 7 beta-hydroxy DHEA, which in turn can be oxidized at the 7 position. Overall well being, particularly in the aged, has been reported to improve with DHEA supplementation, with possible benefits in muscle strength, mood ratings, and memory performance.

Similarly, anxiety and depression can present with multiple overlapping symptoms and stem from the same biological correlates. Treatment is guided by the clinical presentation of these illnesses and our evolving understanding of their pathophysiology. We now know that when treating an individual with co-morbid conditions, effective treatment requires remission of not only the primary disorder but of the co-morbid condition as well.

What is needed therefore are novel treatment methods and compositions to treat symptoms of psychiatric disorders such as stress disorders, anxiety disorders and depression. Ideal compounds are safe and effective with few, if any, side effects.

SUMMARY OF THE INVENTION

The present method addresses a number of problems in the prior art and provides methods of treating symptoms of psychiatric disorders such as stress disorders, anxiety disorders and depression using the DHEA metabolite, 3-acetyl-7-oxo-dehydroepiandrosterone, also known as 7-keto DHEA. The present invention satisfies the need for safe, natural and effective compounds to treat psychiatric disorders.

The DHEA metabolite, 3-acetyl-7-oxo-dehydroepiandrosterone, also known as 7-keto DHEA, is a safe, natural, neuroprotective compound which appears to have benefits as a natural antiglucocorticoid and to improve symptoms of depression, anxiety, trauma, and improve memory and cognitive functioning. There are no reported adverse effects or interactions with any other drug. Besides the psychiatric effects described herein, 7-keto DHEA has other reported effects that include enhanced weight loss, enhanced immune functioning, and thermogenesis. Unlike DHEA, 7-keto DHEA has no androgenic activity, as it is not converted to androgen, and because substitution at the 7 position prevents aromatization, it also cannot be converted to estrogen.

7-keto DHEA appears to have benefits as a natural antiglucocorticoid similar to or perhaps even greater than those of DHEA, which has been shown in numerous studies to be beneficial for memory, cognition, depression, dysthymia, sexual functioning, anxiety, and dissociation, but without the hazards of aromatization to testosterone or estrogen found with DHEA.

7-keto DHEA may also be administered adjunctively with other psychiatric compounds such as analgesic agents, anticonvulsants, anti-anxiety agents, antidepressants, anti-panic agents, antipsychotic agents, mood stabilizing and antimanic agents, bipolar agents, psychostimulants and the like. It is presumed that higher circulating estrogen levels may account for better response of women to serotonergic medications. 7-keto DHEA added to the selective serotonin reuptake inhibitors (SSRI) may help compensate for the relative hypogonadism or lower levels of circulating gonadal steroids in premenopausal and post menopausal women, who make up a very large proportion of patients presenting for treatment for depression.

The patients treated with 7-keto DHEA originally presented with irritability, decreased energy, decreased memory and concentration, depressed or labile mood, decreased libido, anxiety, insomnia, and crying. After treatment with 7-keto DHEA, patients reported improvement in symptoms associated with severe early trauma including dissociation, avoidance and numbing, re-experiencing, hyperarousal, anger, and affective instability. Patients that can be treated with 7-keto DHEA include adults, adolescents and children.

Accordingly, it is an object of the present invention to provide pharmaceutical compositions comprising 7-keto DHEA in an acceptable carrier to treat symptoms of psychiatric disorders such as stress disorders, anxiety disorders and depression.

It is an object of the present invention to provide pharmaceutical compositions comprising 7-keto DHEA in an acceptable carrier to prevent, ameliorate or lessen the severity of symptoms of psychiatric disorders such as stress disorders, anxiety disorders and depression.

It is another object of the present invention to provide pharmaceutical compositions comprising 7-keto DHEA in an acceptable carrier in combination with other psychiatric compounds to treat symptoms of psychiatric disorders such as stress disorders, anxiety disorders and depression.

It is a further object of the present invention to provide treatment protocols and methods to treat symptoms of psychiatric disorders such as stress disorders-including but not limited to PTSD, anxiety disorders and depressive disorders using compositions comprising 7-keto DHEA.

These and other objects, features and advantages of the present invention will become apparent after a review of the following detailed description of the disclosed embodiments and the appended claims.

DETAILED DESCRIPTION OF THE INVENTION

The present invention may be understood more readily by reference to the following detailed description of specific embodiments included herein. Although the present invention has been described with reference to specific details of certain embodiments, thereof, it is not intended that such details should be regarded as limitations upon the scope of the invention. It is understood that methods and materials similar or equivalent to those described herein can be used in the practice or testing of the present method.

The present method provides methods of treating symptoms of psychiatric disorders, such as stress disorders, anxiety disorders and depression, using the DHEA metabolite, 3-acetyl-7-oxo-dehydroepiandrosterone, hereinafter 7-keto DHEA. The present invention satisfies the need for safe, natural and effective compounds to treat psychiatric disorders.

It must be noted that as used in this specification and the appended claims, the terms "a", "an" and "the" as used herein are defined to mean "one or more" and include the plural unless the context is inappropriate. Thus, for example, reference to "an compound" or "a pharmaceutical compound" includes a single compound as well as two or more different compounds in combination, reference to "a carrier" includes mixtures of two or more carriers as well as a single carrier, and the like.

"Carriers" or "vehicles" as used herein refer to conventional pharmaceutically acceptable excipient materials suitable for drug administration, and include any such materials known in the art that are nontoxic and fail to interact with other components of a pharmaceutical composition or drug delivery system in a deleterious manner. Such carriers are commonly known to one of ordinary skill in the art.

The term "pharmaceutically acceptable salts" in this respect, refers to the relatively non-toxic, inorganic and organic salts of the compounds described herein. These salts can be prepared in situ during the final isolation and purification of the compound. Representative salts include the bromide, chloride, hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, naphthylate, mesylate, glucoheptonate, lactobionate, and laurylsulfonate salts and the like. (See, e.g., Berge et al., J. Pharm. Sci., 66:1-19 (1977).) Such salts are commonly known to one of ordinary skill in the art.

By an "effective" amount or a "therapeutically effective amount" of a drug or pharmacologically active agent is meant a nontoxic but sufficient amount of the drug or agent to provide the desired effect. In the combination therapy of the present invention, an "effective amount" of one component of the combination is the amount of that compound that is effective to provide the desired effect when used in combination with the other components of the combination. Further, the term "effective amount of 7-keto DHEA" refers to the amount of 7-keto DHEA composition which, when administered to a human or animal, reduces, ameliorates or prevents symptoms of psychiatric conditions. The amount that is "effective" will vary from subject to subject, depending on the age and general condition of the individual, the particular active agent or agents, and the like. Thus, it is not always possible to specify an exact "effective amount." However, an appropriate "effective" amount in any individual case may be determined by one of ordinary skill in the art using routine experimentation.

The terms "treating" and "treatment" as used herein refer to reduction in severity and/or frequency of symptoms, elimination of symptoms and/or underlying cause, prevention of the occurrence of symptoms and/or their underlying cause, reduction of the severity of psychiatric symptoms developing after a causative stimulus and/or their underlying cause, and improvement or remediation of damage. Thus, for example, "treating" a patient involves prevention of a particular disorder or adverse physiological event in a susceptible individual as well as treatment of a clinically symptomatic individual.

7-Keto DHEA has benefits as a natural antiglucocorticoid similar to or perhaps even greater than those of DHEA but without the hazards of aromatization to testosterone or estrogen found with DHEA. As with DHEA, the exact mechanism of action of 7-keto DHEA is not known, but a putative mechanism is that it may in humans, as in mice, confer neuroprotection and prevent corticosterone-induced neuronal damage. DHEA sulfate levels were measured before treatment since low levels, as described below, are known to correlate with a less resilient response to stress, and the fact that the patients had low levels provided more justification for a treatment that might help reduce their dissociation and dysfunctional responses to stress.

The safety and pharmacokinetics of 7-keto DHEA in healthy male volunteers was reported by Davidson (Davidson et al., Clin Invest Med 2000; 23(5):300-10). There were no differences in clinical laboratory values, reported minor adverse experiences, vital signs, blood chemistry, or urinalysis between treatment and placebo groups. The results showed that 7-keto DHEA is safe and well tolerated in normal healthy men at doses up to 200 mg/d for 4 weeks. Unlike DHEA, 7-keto DHEA is not a precursor for estrogen or testosterone and therefore there are no differences expected in the safety or pharmacokinetics of 7-keto DHEA in women or men.

7-Keto DHEA is produced from the 7-hydroxylated derivative of DHEA, followed by its oxidation. The brain production of the 7-hydroxylated derivative is second to that in the liver, and the $P_{450}7B_1$ containing hippocampus is the major site for 7α-hydroxylation. The 7-hydroxylated derivatives of DHEA were studied for antiglucocorticoid-mediated neuroprotective potencies and both 7 alpha and 7 beta-hydroxy DHEA were efficient in preventing the nuclear uptake of [$^3$H]dexamethasone-activated glucocorticoid receptor in brain cells. Activation of 7 alpha-hydroxylation by contact with astrocytes and after glucocorticoid treatment suggested that the regulated production of 7 alpha-hydroxysteroids was a key event for the neuroprotection conferred by neurosteroids (Morfin and Starka, Int. Rev. Neurobiol. 2001; 46:79-95).

It is important to note that 7-keto DHEA has a major advantage over DHEA in that it is not aromatized to testosterone or estrogen, which can result in risks seen with increased testosterone (such as acne, baldness, hirsutism, voice changes, prostatic effects) or elevated estrogens (such as increased risk of uterine or breast cancer, vaginal bleeding or endometrial hyperplasia, or venous thromboembolism). There are no known important drug interactions, and in a study by Davidson et al., (Clin Invest Med 2000; 23:300-310) 7-keto DHEA caused no side effects or changes in clinical laboratory values. Although there are no case reports of induced mania with 7-keto DHEA, induced mania has been reported with DHEA. None of the 5 patients on 7-keto DHEA treatment reported any negative side effects, and all have continued to show further gains in mental functioning.

In a preferred embodiment, compositions comprising 7-keto DHEA are administered in an effective amount to treat symptoms of a psychiatric condition. In different embodiments, the amount of 7-keto DHEA is between about 1 mg/day and about 2500 mg/day, between about 5 mg/day and about 2000 mg/day, between about 10 mg/day and about 1500 mg/day, between about 10 mg/day and about 1000 mg/day. In one embodiment, the amount of 7-keto DHEA is between about 5 mg/day and about 500 mg/day. In other embodiments 7-keto DHEA is administered at a dose between about 10 mg/day and about 300 mg/day. In still other embodiments, 7-keto DHEA is administered at a dose between about 25 mg/day and about 150 mg/day or between about 25 mg/day and about 200 mg/day.

Adjuvant Drugs

Patients with depression receive only partial improvement from any single pharmacologic agent. Seventy percent of patients with major depression do not experience remission of symptoms after treatment with traditional selective serotonin reuptake inhibitors (SSRIs). Co-administration with 7-keto DHEA will provide greater efficacy and higher rates of full remission, faster onset, and provide a more broad spectrum range of treatment. 7-keto DHEA may also improve sexual functioning for patients on SSRIs.

Greater efficacy, more rapid onset, and the ability to achieve a broader spectrum of effective treatment can result from the co-administration of 7-keto DHEA which acts by a different mechanism than SSRIs. SSRIs can be neuroprotective by increasing brain derived neurotrophic factor. While not wanting to be bound by the following statement, 7-keto DHEA may protect the brain from the damaging effects of stress by functioning as an antiglucocorticoid. 7-keto DHEA may also protect neurons against glutamate-induced, glucocorticoid-mediated damage including inhibition of neurogenesis and cell loss.

Therefore in another embodiment, 7-keto DHEA may be co-administered with other compounds such as, but not limited to, an analgesic, anticonvulsant, antianxiety agent, antidepressant, antipanic agent, antipsychotic agent, anti-bipolar agent, antimanic agent, psychostimulant, a resilience enhancer, or stress reducing compound which may function as an antiglucocorticoid in the brain, a compound which can reduce trauma symptoms, improve attention and concentration, or improve sexual functioning, and the like. These compounds are commonly used to treat psychiatric conditions and their administration routes, dosages and toxicology are known to those of ordinary skill in the art.

As used herein, the term "analgesic agents" includes compounds that have actions on the control and management of pain. Examples of such analgesic agents include, but are not limited to commercially available compounds such as duloxetine HCl (CYMBALTA®, Eli Lilly, Indianapolis, Ill.), pregabalin (LYRICA®, Pfizer, Cambridge, Mass.), gabapentin NEURONTIN®, Pfizer, Cambridge, Mass.), and carbamazepine (TEGRETOL®, Novartis, Basel, CH)

As used herein, the term anticonvulsants includes compounds that prevent the occurrence of epileptic seizures. Many anticonvulsants act by suppressing the rapid and excessive firing of neurons that start a seizure. Examples of such anticonvulsants include, but are not limited to commercially available compounds such as pregabalin (LYRICA®, Pfizer, Cambridge, Mass.), leviracetem (KEPPRA®, UCB Pharma, Smyrna, Ga.), topiramate (TOPOMAX®, Ortho-McNeil, Raritan, N.J.), zonisamide (ZONEGRAN®, Eisai, Teaneck, N.J.), lamotrigine (LAMICTAL®, Glaxo Smith Kline, Philadelphia, Pa.), and oxcarbazepine (TRILEPTAL®, Novartis, Basel, CH).

As used herein, the term antianxiety agents or anxiolytics refers to compounds that are used to treat symptoms of anxiety. Examples of such antianxiety agents include, but are not limited to commercially available compounds such as venlafaxine (EFFEXOR® XR, Wyeth, Madison, N.J.), and sertraline (ZOLOFT®, Pfizer, Cambridge, Mass.)

As used herein, the term antidepressants refers to compounds prescribed to treat or alleviate the symptoms of clinical depression. Examples of such antidepressants agents include, but are not limited to commercially available compounds such as duloxetine HCl (CYMBALTA®, Eli Lilly, Indianapolis, Ill.), venlafaxine (EFFEXOR® XR, Wyeth, Madison, N.J.), sertraline (ZOLOFT, Pfizer, Cambridge, Mass.), buproprion (WELLBUTRIN® SR and XL, Glaxo Smith Kline, Philadelphia, Pa.), and escitalopram oxalate (LEXAPRO®, Forest, Inwood, N.Y.)

As used herein, the term antipanic agents refers to compounds prescribed to treat or alleviate the symptoms of panic attacks. Examples of such antipanic agents include, but are not limited to commercially available compounds such as sertraline (ZOLOFT®, Pfizer, Cambridge, Mass.), fluoxetine (PROZAC®, Eli Lilly, Indianapolis, Ill.) and clonazepim (KLONOPIN®, Roche, Basel, CH).

As used herein, the term antipsychotic agents refers to compounds prescribed to treat or alleviate psychosis. Examples of such antipsychotic agents include, but are not limited to commercially available compounds such as aripiprazole (ABILIFY®, Bristol-Myers Squibb, New York, N.Y.), ziprasidone (GEODON®, Pfizer, Cambridge, Mass.), risperidone (RISPERIDAL™, Janssen, Titusville, N.J.), quetiapine fumarate (SEROQUEL®, Astra Zeneca, Wilmington, Del.), olanzepine (ZYPREXA®, Eli Lilly, Indianapolis, Ill.) and clozapine (CLOZARIL®, Novartis, Basel, CH).

As used herein, the term bipolar agents refers to compounds prescribed to treat or alleviate symptoms of bipolar disorder. Examples of such bipolar agents include, but are not limited to commercially available compounds such as divalproex sodium, (DEPAKOTE®, Abbott), aripiprazole (ABILIFY®, Bristol-Myers Squibb, New York, N.Y.), ziprasidone (GEODON®, Pfizer, Cambridge, Mass.), quetiapine fumarate (SEROQUEL®, Astra Zeneca, Wilmington, Del.), olanzepine (ZYPREXA®, Eli Lilly, Indianapolis, Ill.), lamotrigine (LAMICTAL®, Glaxo Smith Kline, Philadelphia, Pa.), fluoxetine (PROZAC®, Eli Lilly, Indianapolis, Ill.), olanzapine (SYMBYAX®, Eli Lilly, Indianapolis, Ill.), and carbamazepine (EQUETRO™, Shire Pharmaceuticals, Wayne, Pa.)

As used herein, the term psychostimulants refers to controlled, amphetamine-like drugs that are currently approved only for the treatment of psychiatric conditions such as attention-deficit/hyperactivity disorder (ADHD) and narcolepsy. Examples of such psychostimulants include, but are not limited to commercially available compounds such as amphetamine mixed salts (ADDERALL®, Shire Pharmaceuticals, Wayne, Pa.), dextroamphetamine sulfate (DEXEDRINE®, Glaxo Smith Kline, Philadelphia, Pa.), methylphenidate HCl (CONCERTA® McNeil-PPC, Fort Washington, Pa.), and modafinil (PROVIGIL®, Cephalon)

The compounds useful in the present methods, or pharmaceutically acceptable salts thereof, can be delivered to a patient using a wide variety of routes or modes of administration. Suitable routes of administration include, but are not limited to, inhalation, cutaneous, topical, transdermal, oral, rectal, vaginal, transmucosal, intestinal and parenteral administration, including intramuscular, subcutaneous and intravenous injections. Tablets, capsules, creams, patches and suppositories may be used as delivery vehicles.

The term "pharmaceutically acceptable salt" means those salts which retain the biological effectiveness and properties of the compounds used in the present methods, and which are not biologically or otherwise undesirable. Such salts may be prepared from inorganic and organic bases. Salts derived from inorganic bases include, but are not limited to, the sodium, potassium, lithium, ammonium, calcium, and magnesium salts. Salts derived from organic bases include, but are not limited to, salts of primary, secondary and tertiary amines, substituted amines including naturally-occurring substituted amines, and cyclic amines, including isopropylamine, trimethylamine, diethylamine, triethylamine, tripropylamine, ethanolamine, 2-dimethylaminoethanol, tromethanine, lysine, arginine, histidine, caffeine, procaine, hydrabamine, choline, betaine, ethylenediamine, glucosamine, N-alkylglucamines, theobromine, purines, piperazine, piperidine, and N-ethylpiperidine. It should also be understood that other carboxylic acid derivatives would be useful in the practice of this method, for example carboxylic acid amides, including carboxamides, lower alkyl carboxamides, di(lower alkyl) carboxamides, and the like.

The compounds, or pharmaceutically acceptable salts thereof, may be administered singly, in combination with other compounds, and/or in cocktails combined with other therapeutic agents. Of course, the choice of therapeutic agents that can be co-administered with the compounds of the present method will depend, in part, on the condition being treated.

The active compounds (or pharmaceutically acceptable salts thereof) may be administered per se or in the form of a pharmaceutical composition wherein the active compound(s) is in admixture or mixture with one or more pharmaceutically acceptable carriers, excipients or diluents. Pharmaceutical compositions for use in accordance with the present method may be formulated in conventional manner using one or more physiologically acceptable carriers including excipients and auxiliaries which facilitate processing of the active compounds into preparations which can be used pharmaceutically. Proper formulation is dependent upon the route of administration chosen.

For injection, the compounds may be formulated in aqueous solutions, preferably in physiologically compatible buffers such as Hanks's solution, Ringer's solution, or physiological saline buffer. For transmucosal administration, penetrants appropriate to the barrier to be permeated are used in the formulation. Such penetrants are generally known in the art.

For oral administration, the compounds can be formulated readily by combining the active compound(s) with pharmaceutically acceptable carriers well known in the art. Such carriers enable the compounds of the present method to be formulated as tablets, pills, dragees, capsules, liquids, gels, syrups, slurries, suspensions and the like, for oral ingestion by a patient to be treated. Pharmaceutical preparations for oral use can be obtained as a solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores can be provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

In one embodiment, capsules of 7-keto DHEA are provided for oral administration. Capsules of 25 mg, 50 mg and 100 mg are commercially available from vendors including but not limited to Smart Nutrition in San Diego, Calif., Now Foods in Bloomingdale, Ill., Puritan Pride in Oakdale N.Y. and Life Extension in Hollywood, Fla.

For administration orally, the compounds may be formulated as a sustained release preparation. Numerous techniques for formulating sustained release preparations are described in the following references: U.S. Pat. Nos. 4,891,223; 6,004,582; 5,397,574; 5,419,917; 5,458,005; 5,458,887; 5,458,888; 5,472,708; 6,106,862; 6,103,263; 6,099,862; 6,099,859; 6,096,340; 6,077,541; 5,916,595; 5,837,379; 5,834,023; 5,885,616; 5,456,921; 5,603,956; 5,512,297; 5,399,362; 5,399,359; 5,399,358; 5,725,883; 5,773,025; 6,110,498; 5,952,004; 5,912,013; 5,897,876; 5,824,638; 5,464,633; 5,422,123; and 4,839,177; and WO 98/47491.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, the compositions may take the form of tablets or lozenges formulated in conventional manner.

For administration by inhalation, the active compound(s) may be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the active compound(s) may be in powder form for formulation with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation or transcutaneous delivery (for example subcutaneously or intramuscularly), intramuscular injection or a transdermal patch. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

A further embodiment of the present methods is related to a nanoparticle. The compounds described herein may be incorporated into the nanoparticle. The nanoparticle within the scope of the invention is meant to include particles at the single molecule level as well as those aggregates of particles that exhibit microscopic properties. Methods of using and making the above-mentioned nanoparticle can be found in the art (U.S. Pat. Nos. 6,395,253, 6,387,329, 6,383,500, 6,361,944, 6,350,515, 6,333,051, 6,323,989, 6,316,029, 6,312,731, 6,306,610, 6,288,040, 6,272,262, 6,268,222, 6,265,546, 6,262,129, 6,262,032, 6,248,724, 6,217,912, 6,217,901, 6,217,864, 6,214,560, 6,187,559, 6,180,415, 6,159,445, 6,149,868, 6,121,005, 6,086,881, 6,007,845, 6,002,817, 5,985,353, 5,981,467, 5,962,566, 5,925,564, 5,904,936, 5,856,435, 5,792,751, 5,789,375, 5,770,580, 5,756,264, 5,705,585, 5,702,727, and 5,686,113).

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Pharmaceutical compositions suitable for use in the present methods include compositions wherein the active ingredient is contained in a therapeutically effective amount, i.e., in an amount effective to achieve therapeutic benefit, as previously discussed. Of course, the actual amount effective for a particular application will depend, inter alia, on the condition being treated and the route of administration. Determination of an effective amount is well within the capabilities of those skilled in the art, especially in light of the disclosure herein.

Therapeutically effective amounts for use in humans can be determined from animal models. For example, a dose for humans can be formulated to achieve circulating concentration that has been found to be effective in animals.

Methods of Use

In one embodiment the method comprises using 7-keto DHEA to treat psychiatric conditions. The method comprises administering an effective amount of 7-keto DHEA to an individual in need of treatment to reduce symptoms of the psychiatric condition. The individual is first evaluated for characteristics to help determine if they would be a suitable candidate for the treatment. Treatment includes 7-keto DHEA alone or in combination with other pharmaceutical compounds described above to reduce symptoms of the psychiatric condition. Compounds may be co-administered or administered sequentially to treat the psychiatric condition. Treatment may continue until the symptoms subside or treatment may continue beyond the point that symptoms subside if there is reason to believe that a reoccurrence of the condition will happen.

Many different stimuli may cause stress, PTSD, anxiety depression and other psychiatric conditions, for example, war, accidents, catastrophes, torture, crime, rape, abuse, and death of a loved one. Soldiers, emergency personnel, police, firefighters, crime victims, prisoners, family members and numerous other individuals may exhibit these psychiatric conditions.

In another embodiment, 7-keto DHEA is administered prophylactically to prevent the onset of a psychiatric condition such as, but not limited to PTSD. 7-keto DHEA could be rapidly and easily administered to patients who have been subject to trauma or other hazardous stimulus, in order to prevent the development of the psychiatric condition. In one embodiment, 7-keto DHEA reduces symptoms of trauma and stress and is used in the immediate aftermath of trauma exposure to ameliorate acute symptoms and to prevent the later development of severe and debilitating chronic PTSD. The 7-keto DHEA treatment either alone or with an adjunct compound is easily administered in the Emergency Department, accident sites or any acute care setting to an individual presenting after trauma before PTSD would otherwise develop.

Psychiatric conditions include, but are not limited to, stress-related mental conditions such as PTSD, combat operational stress reaction (COSR), combat stress injury (CSI), acute stress disorder, depression, anxiety disorders, and dissociative identity disorder, and to treat the co-morbid mental problems that occur with these disorders including improving memory (both explicit and working memory), cognitive functioning, dissociation, energy, libido, arousal, and sexual dysfunction, insomnia, nightmares, somatization, chronic pain, dysthymia, anxiety, irritability, impulsivity, aggression and psychosis, as well as headaches associated with stress and autoimmune disorders. Also contemplated is the use of 7-keto DHEA alone or as an adjunctive agent for treating treatment resistant depression, major depression, depression with comorbid anxiety, depressive disorder not otherwise specified (NOS), unipolar and bipolar depression associated with the menopausal transition, bipolar I and II disorders, cyclothymic disorder, dysthymic disorder, mood disorder NOS, borderline personality disorder, anxiety disorders including panic disorder, generalized anxiety disorder, and social anxiety disorder, PTSD, obsessive-compulsive disorder, somatization disorder, pain disorder, psychotic depression, as an anti-psychotic medication, for treating schizophrenia, for reducing suicidal behavior and ideation, for providing enhanced resiliency for coping with trauma and stress, including improving the immune response to stress, and for improving libido, arousal, and sexual functioning in general, and for improving libido, arousal, and sexual functioning for patients on SSRIs, antipsychotics, or medications which can interfere with sexual functioning.

Administration Protocols

Administration protocols are generally tailored to the needs of the individual in need of treatment and the nature of the psychiatric condition to be treated. In a preferred embodiment, 7-keto DHEA is administered in an effective amount to treat symptoms of a psychiatric condition.

Compositions comprising 7-keto DHEA are administered in an effective amount to treat symptoms of a psychiatric condition. In different embodiments, the amount of 7-keto DHEA is between about 1 mg/day and about 2500 mg/day, between about 5 mg/day and about 2000 mg/day, between about 10 mg/day and about 1500 mg/day, between about 10 mg/day and about 1000 mg/day. In one embodiment, the amount of 7-keto DHEA is between about 5 mg/day and about 500 mg/day. In other embodiments 7-keto DHEA is administered at a dose between about 10 mg/day and about 300 mg/day. In still other embodiments, 7-keto DHEA is administered at a dose between about 25 mg/day and about 150 mg/day or between about 25 mg/day and about 200 mg/day. These dosages and dosage ranges are appropriate for different routes of administration, particularly the oral route of administration.

In one embodiment, a dose of 7-keto DHEA is administered at a starting dose of 25 mg daily. In another embodiment, a dose of 7-keto DHEA is administered at a starting dose of 50 mg daily. The daily dosage may be increased 25 mg or higher to improve symptoms of the condition if needed. In one embodiment, dosing is increased every 1 or 2 weeks as needed by about 25 mg daily up to about 200 mg or about 300 mg per day. The 7-keto DHEA may be administered as a single dose per day or in divided doses throughout the day. In one embodiment, the most profound psychiatric benefits occur with the drug administered as a single dose in the morning. The decision to increase or decrease the dose is based on clinical response. A person of ordinary skill in the art is capable of making such decisions based on observations of clinical response. Typically treatment may last days, weeks or months depending on the individual and the nature of the condition to be treated. As shown in the following examples, some patients who respond to 7-keto DHEA treatment and have shown improvement in mental functioning have continued on 7-keto DHEA long term.

The following examples will serve to further illustrate the present methods without, at the same time, constituting any limitation thereof. It is to be clearly understood that resort may be had to various embodiments, modifications and equivalents thereof which, after reading the description herein, may suggest themselves to those skilled in the art without departing from the spirit of the invention.

EXAMPLE 1

7-Keto DHEA for Healing Treatment-Resistant Posttraumatic Stress Disorder in Women Five Case Reports The following case reports are of 5 women with severe chronic PTSD resulting from severe early abuse who continued to be highly symptomatic despite receiving extensive psychotherapy and years of psychopharmacologic treatment. All 5 of these treatment-resistant patients experienced a rapid and substantial reduction in their trauma and affective symptoms after starting on treatment with 7-keto DHEA. The improvements in these symptoms not only were subjective and objective, but also manifested in significant and rapid benefits in vocational and interpersonal functioning.

Case 1. Ms. A., a 43-year-old woman with chronic severe PTSD associated with a history of severe physical and sexual abuse beginning in childhood (age 4), had remained highly symptomatic despite individual and group cognitive-behavioral therapy (CBT) for 4 and a half years and trials of fluoxetine 60 mg/day, to which bupropion 150 mg/day and then sertraline 100 mg/day were added. She did not respond to prior trials of olanzapine, quetiapine, or venlafaxine and could not tolerate mirtazapine.

Ms. A. had co-morbid diagnoses of DSM-IV bipolar 11 disorder and dissociative identity disorder as well as hepatitis C virus and type I (insulin-dependent) diabetes mellitus. Prior to starting on 7-keto DHEA treatment, her DHEA level was 70 µg/dL, (in the lowest quartile of the normal range of 32-240 µg/dL).

Her symptoms included hypervigilance, constant anxiety, fearfulness, flashbacks, frequent dissociative experiences, affective lability, decreased libido, irritability, avoidance, numbing, and frequent inability to "feel" her feelings. Ms. A.'s dissociative symptoms, fearfulness, and mental anguish were so severe that several other patients in the trauma program were worried about her and requested help for her.

Ms. A. was an existing patient for 4 years prior to starting her on treatment with 7-keto DHEA but was unable to develop a good therapeutic relationship because Ms. A. was so fearful and avoidant she would miss many sessions. She was so fragile and frightened she would frequently dissociate during sessions and forget what had been discussed. Patient was directed to take 25 mg/day of 7-keto DHEA. The formulation of 7-keto DHEA is made by Smart Nutrition (San Diego, Calif.) in the form of capsules containing 25 mg of the active compound. After the first week of 7-keto DHEA therapy, Ms. A. stopped feeling so fearful, stopped dissociating, was much more communicative, and related better. She reported feeling "more organized, more present" and being able to enjoy socializing "with a significant lessening of constant fear and self-criticism."

Anxiety and feelings of detachment, though markedly diminished, were still present, so her dosage of 7-keto DHEA was increased to 50 mg daily. Ms. A described even further improvement after this dosage increase. She said this dosage gave her even more mental clarity and energy us well us better memory and allowed her to feel "more centered" and able to "feel my feelings" without dissociating. After 3 weeks on a 50-mg/day dose, she said, "I am more aware and accepting of my own and other people's issues. It's like I was sleeping and I woke up," She stopped having nightmares, had much better concentration, functioned better at work and in social situations, had more stable mood (she said that "the high is not so high and the low is not so low"), and for the first time was able to handle stressful situations constructively and independently. She said she went from having no libido to some libido and was now interested in dating, after years of avoiding men. Ms. A. now has an excellent therapeutic relationship with her psychiatrist, no longer avoids treatment, and recently said, "This is the first time I realize why people want to be alive."

Case 2. Ms. B., a 55-year-old woman with chronic severe PTSD (DSM-IV) associated with a history of severe childhood physical and sexual abuse, had remained highly symptomatic despite undergoing one and a half years of individual and group CBT and receiving paroxetine up to 30 mg daily, from other practitioners, for more than 4 years. She had a history of failed trials on fluoxetine and sertraline; both drugs caused her to be agitated and irritable. She wished to be tapered off paroxetine because she had gained 40 lb, and after becoming obese, she also became hypertensive. Ms. B. also said she felt that paroxetine was not helping her chronic severe anxiety and irritability. Although her paroxetine dosage was tapered to 5 mg every other day, and lamotrigine 100 mg and topiramate 75 mg were administered daily, she remained highly symptomatic.

Prior to starting on 7-keto DHEA therapy, Ms. B. had severe mood liability, alternating between irritability and fearfulness; was chronically anxious and depressed; and reported feeling helpless and "alone." She was fired from her last job due to non-attendance and was too agitated, irritable, and labile to function at any job. She had frequent flashbacks of childhood physical abuse and intrusive thoughts regarding sexual abuse. Ms. B.'s other symptoms of PTSD included avoidance and detachment from most people, social isolation, and periods of numbing and dissociation during which she described herself as feeling very vulnerable and stressed to the point of not even being able to feel her feelings. Her co-morbid diagnoses were bipolar disorder not otherwise specified (DSM-IV), opioid dependence in full remission for 15 years, and hypertension. Her DHEA sulfate level of 34 µg/dL was near the bottom of the normal range (32-240 µg/dL).

Within a few days after starting treatment with 7-keto DHEA 25 mg daily, Ms. B. reported feeling much better. She was calmer, she experienced much less anger and irritability, and her mood became more stable. She said she was finding it easier to do well in school because she was better able to focus when studying and attending class, adding, "Now I'm better able to remember what I've read." Ms. B. also reported having an easier time socializing and a renewed interest in sex after having had no sexual interest at all for a month. Within 2 weeks after starting on 7-keto DHEA, she felt calm and centered enough to return to work, attended a job interview in which she performed very well, and was quickly offered a job at a local hospital.

Case 3. Ms. F., a 52-year-old woman with chronic severe PTSD associated with a history of severe physical and sexual abuse beginning in childhood (age 5), had remained highly symptomatic despite attending group and individual CBT sessions for 17 months and receiving treatment with sertraline 250 mg and topiramate 225 mg daily and quetiapine 75-100 mg at bedtime. She was also on a methadone maintenance dose of 60 mg daily. Her symptoms included irritability, mood lability, crying, difficulty sleeping, nightmares from which she would wake up screaming, flashbacks, hypervigilance, and frequently feeling fatigued, depressed, and lonely. Her affect was constricted and distant, she was quick to feel offended or alienated, and she reported feeling detached from others.

Ms. F.'s co-morbid diagnoses were major depressive disorder, recurrent, moderate, rheumatoid arthritis, hepatitis B, gastritis, asthma, and obesity. Her DHEA sulfate level was low (19.8 µg/dL; normal range, 42-290 µg/dL).

After 4 days on treatment with 7-keto DHEA 25 mg daily, Ms. F. said she felt better and was no longer getting anxious and overwhelmed by stressful events. She also reported having better memory; i.e., she found appointments easier to remember.

Ms. F. appeared better socially related, was less guarded and pessimistic, had less constricted affect, maintained better eye contact, and was more productive and open in her communication. Seven days after starting on 7-keto DHEA treatment, she reported having fewer nightmares and flashbacks and that, when they occurred, they were less frightening and upsetting. She also said she felt more relaxed and was no longer crying or getting very upset when she experienced anger.

Case 4. Ms. D., a 59-year-old woman, was in psychiatric treatment for over 25 years, including a long course of psychoanalysis and 2 years of CBT. She had been treated with adequate trials of 2 tricyclic antidepressants, 3 SSRIs, venlafaxine, 2 monoamine oxidase inhibitors, 3 anticonvulsants, many typical and atypical antipsychotics, lithium, bupropion, trazodone, and nefazodone. The only medications that gave her some relief from anxiety, depression, and agitation were occasional lorazepam 1 mg p.r.n. and aripiprazole 2.5 mg daily. Pemoline 75 mg daily and phentermine 30 mg daily gave her enough energy to function. Methylphenidate, dextroamphetamine, and other stimulants had been tried but all made her anxiety worse.

In spite of all of the treatment she had received, Ms. D. continued to experience severe symptoms of anxiety, fearfulness, irritability, and difficulty concentrating. These symptoms interfered with her ability to socialize with friends and family, learn new information, and integrate and retain the skills she was being taught in CBT. She was referred 14 years ago for treatment-resistant depression but, as more clinical information became available, was re-diagnosed by her treating psychiatrist and psychologist as having PTSD with dissociative identity disorder (both DSM-IV). She suffered from physical, emotional, and sexual abuse as a child but would never discuss details because it was too disturbing to her.

She was treated with 7-keto DHEA 50 mg for 6 weeks, which led to some improvement in daily functioning and more positive affect. The dose was increased to 100 mg for 6 weeks to achieve more significant improvements. She became much more social and said she was able to read and enjoy complex intellectual material for the first time since childhood. Ms. D. also gained the ability to use skills for emotion regulation from the dialectic behavior therapy that she had been receiving (with a Ph.D.-level psychologist experienced in treatment of PTSD) for the previous 2 years. Her dose was increased to 150 mg daily and she continued to improve.

Case 5. Ms. E., a 55-year-old woman referred by her psychiatrist, had a lifelong history of anxiety, PTSD, dissociative identity disorder, panic attacks for more than 30 years, agoraphobia, frequent visits to emergency rooms with conversion symptoms such as uncontrollable pelvic thrusting movements, social anxiety disorder, irritability, depression, and lack of energy and libido. She was raised in a rigid, excessively strict Protestant family and had a history of childhood physical and verbal abuse. She refused to discuss possible sexual abuse.

Her symptoms persisted in spite of psychotherapy for more than 15 years and numerous trials on medications. She was treated with sertraline for 6 years (1994-2000) with minimal benefit. Venlafaxine was slightly helpful, but, while receiving a dose of 300 mg daily, she became overly activated and venlafaxine treatment had to be stopped. Ziprasidone and prochlorperazine caused severe dystonic-like reactions. Topiramate caused severe cognitive dysfunction. Quetiapine caused severe sedation, and aripiprazole caused a 30-lb weight gain.

Fearful of conventional psychotropic medication, and having developed type 2 (adult-onset) diabetes mellitus, Ms. E. requested alternative approaches. She was begun on treatment with 7-keto DHEA 25 mg daily, raised after 1 week to 50 mg, and after 4 weeks to 75 mg daily to achieve fuller remission. She reported feeling calmer and being better able to deal with the stress of her mother's death and with settling the estate, as well as experiencing less need to overeat to soothe herself. She said she had more focus, had more creative ability in her writing, and no longer needed to talk to herself when alone. She also began to exercise and lose weight. Ms. E said that she felt this was the first medication ever to help her.

DISCUSSION

While there have been a number of articles written about DHEA, this is the first report of the benefits of 7-keto DHEA in treating symptoms associated with severe early trauma, including dissociation, avoidance and numbing, re-experiencing, hyperarousal, anger, and affective instability. The outcome of this case series offers evidence that 7-keto DHEA is beneficial in treating patients with histories of severe early trauma and persistent refractory PTSD. In the first 4 cases, 7-keto DHEA was added as an adjunct to the patients' other medications. In case 5, 7-keto DHEA was used as a single agent.

EXAMPLE 2

7-Keto DHEA for Healing Treatment-Resistant Posttraumatic Stress Disorder, Panic Disorder, Anxiety, Depression and Other Conditions in Male and Female Patients Sixteen Case Reports In all the patient reports that follow, 7-keto DHEA was administered orally. The medications taken by the patients were continued unchanged during 7-keto DHEA administration. The patients generally reported the results to the clinician at the office visit following the administration of 7-keto DHEA.

Patient 1 A 51 year old male with PTSD and Generalized Anxiety Disorder following a street mugging that caused head trauma and concussion. Patient had less anxiety within 2 days on 7-keto DHEA—25 mg/day.

Patient 2 A 58 year old female with PTSD, chronic anxiety and Major depression had less anxiety and depression on 7-keto DHEA—50 mg/day.

Patient 3 A 45 year old female with Panic Disorder and Generalized Anxiety Disorder had less anxiety and panic on 7-keto DHEA—25 mg/day.

Patient 4 A 57 year old female with PTSD and Generalized Anxiety Disorder and Bipolar Depression was less anxious and depressed on 7-keto DHEA—25 mg/day.

Patient 5 A 39 year old female with Bipolar Depression and PTSD was less anxious and depressed on 7-keto DHEA—25 mg/day.

Patient 6 A 52 year old female with Tourette's Syndrome and chronic dysthymia, anxiety, was calmer and in a better mood on 7-keto DHEA—50 mg/day).

Patient 7 A 41 year old female with Ankylosing Spondylitis, chronic pain, and depression was calmer and less depressed on 7-keto DHEA—25 mg/day.

Patient 8 A 46 year old female with Dissociative Disorder, PTSD, Major Depression and Dependent Personality Disorder improved on 7-keto DHEA—25 mg/day, and reported less anxiety and dissociation.

Patient 9 A 46 year old female with PTSD, Generalized Anxiety Disorder and Major Depression was less anxious and depressed on 7-keto DHEA—25 to 50 mg/day.

Patient 10 A 63 year old female with Bipolar Depression and PTSD was less anxious and depressed on 7-keto DHEA—25 mg/day.

Patient 11 A 59 year old female with Bipolar Depression and PTSD was less anxious on 7-keto DHEA—25 mg/day.

Patient 12 A 59 year old female with Bipolar Depression and PTSD was less anxious on 7-keto DHEA—25 mg/day.

Patient 13 A 62 year old female with PTSD and Major Depression was less depressed and anxious on 7-keto DHEA—50 mg/day.

Patient 14 A 51 year old female with Adult Attention Deficit Hyperactivity Disorder, Bereavement, and PTSD was less irritable and anxious on 7-keto DHEA—25 mg/day.

Patient 15 A 49 year old female with Generalized Anxiety Disorder had lower anxiety and better mood on 7-keto DHEA—25 mg/day.

Patient 16 A 49 year old female with Generalized Anxiety Disorder and Fibromyalgia had lower anxiety and irritability on 7-keto DHEA—25 mg/day.

EXAMPLE 3

7-Keto DHEA for Healing Treatment-Resistant Posttraumatic Stress Disorder, Panic Disorder, Anxiety, Depression and Other Conditions in Male and Female Patients Eight Case Reports Patient 1 A 44 year old married female with lifelong depression, winter worsening, PMDD (premenstrual dysphoric disorder), and sexual PTSD was intolerant of Paxil, Zoloft, Prozac, Lexapro, venlafaxine, Wellbutrin and S-adenosylmethionine (SAMe), improved after administration of 7-keto DHEA 75 mg/day and remained well about 2 years after treatment.

Patient 2 A 61 year old married female was anxious all her life, hypertensive, fragile, had 4 years of depression due to stress and received 12 years of psychoanalysis. She could not tolerate Zoloft, Celexa, Wellbutrin, Effexor, Cymbalta, Remeron, and SAMe. Rhodiola helped to an extent, however administration of 7-keto DHEA 50 mg/day was very effective and she remained well for 1¾ years.

Patient 3 A 55 year old married female with lifelong generalized anxiety disorder (GAD), panic disorder, and fibromyalgia syndrome/chronic fatigue syndrome (CFS) for 15 years, failed or couldn't tolerate three SSRIs (selective serotonin reuptake inhibitors), two tricyclic antidepressants, valproate, and lamotrigine (LMT Lamictal). She was partially helped by Remeron and SAMe. Administration of 7-keto DHEA 50 mg/day provided improvement in her symptoms and she has remained well for about 1 year.

Patient 4 A 57 year old female with severe dissociative identity disorder (DID) and fibromyalgia syndrome and Bipolar Disorder, failed every anticonvulsant drug, atypical antipsychotic, antidepressant, many electroconvulsive therapies, multiple emergency room visits and hospitalizations, and was considered a treatment failure. She was administered 7-keto DHEA (200 mg/day), and has been well for a year and is able to read and function.

Patient 5 A 59 year old female, married therapist with PTSD and bipolar 2 disorder who failed many antidepressants, anticonvulsant drugs, and atypical antipsychotics, partially improved on lamotrigine (LMT Lamictal)/Zoloft. Administration of 7-keto DHEA 50 mg/day in the summer 100 mg/day in the winter was very effective and she has remained well for 2 years.

Patient 6 A 64 year old female who was a divorced mother failed most antidepressants, atypical antipsychotics and electroconvulsive therapy, partially responded to venlafaxine (but did not like the side effects) and Abilify in the past. Administration of 7-keto DHEA had tremendous positive effects in 1 week and she has remained well for about 1 year. She partially relapsed following a stressful episode (breast cancer). The dosage of 7-keto DHEA was then increased from 100 mg/day to 300 mg/day with good results.

Patient 7 A 58 year old married therapist with lifelong depression, sexual PTSD and fibromyalgia syndrome/chronic fatigue syndrome) for about 10 years, failed or was intolerant of many antidepressants. She partially responded to Doxepin but was intolerant of the side effects. SAMe made the Doxepin work better but 7 keto-DHEA (200 mg/day) provided a significant benefit and the patient has remained well for 9 months.

Patient 8 A 58 year old lawyer with cognitive impairment in thinking and memory occurring after cancer chemotherapy (chemobrain) and chronic fatigue syndrome/Fibromyalgia after treatment for breast cancer; failed to respond to several SSRIs and alternative treatments. Administration of 7-keto DHEA 50 mg/day provided significant improvement.

EXAMPLE 4

Treatment of Trauma Victims with 7-Keto DHEA

Trauma victims following a terrorist attack are administered 7-keto DHEA (50 or 75 mg/day by mouth) or placebo for 2 to 6 weeks immediately following the incident. Patients receiving 7-keto DHEA display a reduction in PTSD, depression and stress-related emotional conditions compared to patients receiving placebo.

EXAMPLE 5

Treatment of Trauma Victims with 7-Keto DHEA

Trauma victims with PTSD or depression following the stress-inducing event are administered 7-keto DHEA (75 mg/day by mouth) or placebo for 1 to 6 months. Patients receiving 7-keto DHEA display a reduction in their PTSD depression and stress-related emotional conditions compared to patients receiving placebo.

EXAMPLE 6

Treatment of Trauma Victims with 7-Keto DHEA

Trauma victims with PTSD or depression following a stress-inducing event and other trauma patients without PTSD or depression after the stress-inducing event are administered 7-keto DHEA (25-75 mg/day by mouth) or placebo for 1 to 6 months. Patients with PTSD or depression receiving 7-keto DHEA display a reduction in one or more stress-related physiologic measures (pain, headaches, hypertension, alcohol and substance abuse, work days lost to illness, and cardiac events) compared to patients receiving placebo. Patients without PTSD or depression and receiving 7-keto DHEA after the stress-inducing event display a reduction in one or more stress-related physiologic measures (pain, headaches, hypertension, alcohol and substance abuse, work days lost to illness and cardiac events) compared to patients receiving placebo.

Various modifications and variations to the described embodiments of the inventions will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes of carrying out the invention which are obvious to those skilled in the art are intended to be covered by the present invention. All publications, patent applications, patents, and other references mentioned herein are incorporated by reference in their entirety.

We claim:

1. A method for treating a psychiatric condition comprising administering an effective amount of a composition comprising 7-keto DHEA in a pharmaceutically acceptable carrier to an individual in need of treatment to reduce symptoms of the psychiatric condition, wherein the psychiatric condition is post-traumatic stress disorder, combat operational stress reaction, combat stress injury, acute stress disorder, dissociative identity disorder, dissociation, or nightmares.

2. The method of claim 1, further comprising administering a psychoactive compound.

3. The method of claim 1, wherein the effective amount of 7-keto DHEA is between about 1 mg/day and about 2500 mg/day, between about 5 mg/day and about 2000 mg/day, between about 10 mg/day and about 1500 mg/day, or between about 10 mg/day and about 1000 mg/day.

4. The method of claim 1, wherein the administration is oral, topical or parenteral.

5. The method of claim 1, wherein the administration is once per day.

6. The method of claim 1, wherein the psychiatric condition is post-traumatic stress disorder, or dissociative identity disorder, or a combination thereof.

7. A method to ameliorate the severity of symptoms of a psychiatric condition comprising administering an effective amount of a composition comprising 7-keto DHEA in a pharmaceutically acceptable carrier to an individual before the appearance of the symptoms in the individual, wherein the psychiatric condition is post-traumatic stress disorder, combat operational stress reaction, combat stress injury, acute stress disorder, dissociative identity disorder, dissociation, or nightmares.

8. The method of claim 7, further comprising administering a psychoactive compound.

9. The method of claim 7, wherein the effective amount of 7-keto DHEA is between about 1 mg/day and about 2500 mg/day, between about 5 mg/day and about 2000 mg/day, between about 10 mg/day and about 1500 mg/day, or between about 10 mg/day and about 1000 mg/day.

10. The method of claim 7, wherein the administration is oral, topical or parenteral.

11. The method of claim 7, wherein the administration is once per day.

12. The method of claim 7, wherein the psychiatric condition is post-traumatic stress disorder, or dissociative identity disorder, or a combination thereof.

* * * * *